United States Patent [19]

Swanton, Jr.

[11] Patent Number: 4,777,346

[45] Date of Patent: Oct. 11, 1988

[54] ELECTRICALLY HEATED THERAPEUTIC PILLOW

[76] Inventor: Joseph E. Swanton, Jr., 719 4th Ave., NE., Hickory, N.C. 28601

[21] Appl. No.: 911,119

[22] Filed: Sep. 24, 1986

[51] Int. Cl.$^4$ .............. H05B 1/02; H05B 3/54; A61F 7/04; H01C 10/10

[52] U.S. Cl. .................. 219/313; 128/403; 219/201; 219/327; 219/496; 219/509; 338/114; 383/901

[58] Field of Search ............... 219/200, 201, 313, 528, 219/211, 212, 527, 327, 509, 496; 128/402, 403, 399, 400; 383/901; 338/114

[56] References Cited

U.S. PATENT DOCUMENTS

| | | | |
|---|---|---|---|
| 2,072,564 | 3/1937 | May | 383/901 |
| 2,114,396 | 4/1938 | McFarlan et al. | 219/549 X |
| 2,223,154 | 11/1940 | Thornton-Norris | 219/313 |
| 2,294,010 | 8/1942 | Van Daam | 219/313 |
| 2,445,660 | 7/1948 | Bruestle | 338/114 |
| 3,014,117 | 12/1961 | Madding | 128/403 X |
| 3,386,067 | 5/1968 | Costamzo | 338/114 X |
| 3,885,403 | 5/1975 | Spencer | 128/403 X |
| 4,201,218 | 5/1980 | Feldman et al. | 219/313 X |
| 4,204,110 | 5/1980 | Smit et al. | 219/201 X |

Primary Examiner—Anthony Bartis
Attorney, Agent, or Firm—Gilden & Israel

[57] ABSTRACT

A liquid or gel filled pillow utilized for therapeutic purposes is formed from a pair of flexible casing of plastic or the like, one within the other, and being separated by a compressible electrically conductive foam material having a high resistance in its uncompressed slate and a low resistance when compressed. The facing surfaces of the casings are coated with a layer of highly conductive material in electrical contact with the foam. The inner casing is provided with a thermostatically controlled heating element for heating the liquid or gel contained therein. One terminal of the heating element is connected to the power supply through the conductive layers foam so that upon compression of the foam, as would be occasioned by a patient laying his head upon the pillow, there will result an electric current flow to the heating element due to the lowered electrical resistance of the foam. Upon removal of the compressive force to the pillow, the foam reverts to its high resistance uncompressed state thereby automatically terminating electric current flow to the heating element.

1 Claim, 3 Drawing Sheets

ELECTRICALLY HEATED THERAPEUTIC PILLOW

BACKGROUND OF THE INVENTION

1. Field of the Invention

The present invention relates to fluid filled pillows, and more particularly pertains to pillows having heating means so as to permit their use for therapeutic purposes.

2. Description of the Prior Art

Various patient treatment pads and other devices for applying heat therapy are well known in the art. Further, there have been some inventions directed to the construction of heating pads which are designed for applying heat therapy to a user's head. For example, U.S. Pat. No. 2,469,771, which issued to T. Jepson on May 10, 1949, discloses a facial hydrotherapeutic device attachable to a user's face and having a flow of heated fluid directed therethrough. This device requires a tubular arrangement for attachment to a supply of flowing heated water, or some similar heated fluid, and is not designed to permit a user to recline thereon.

A similar approach to the need for applying therapeutic heat to a patient's head is found in U.S. Pat. No. 2,299,162, which issued to L. Marick on Oct. 20, 1942. The Marick device is attachable by straps to the face of a patient and effectively comprises an electrically heated sinus pad. No warmed fluids are used, nor is the device functional as a pillow or some similar device on which the patient could recline.

While the above-described therapeutic heating devices are funtional for their intended purposes, it can be appreciated that they are designed for very specific applications and are not particularly well designed for long term use, as could be occasioned by a person reclining thereon. Further, the manner of attaching these devices to a patient's head by necessity limits the area of heat application to the patient's face, whereby no heat application can be afforded to other parts of the patient's head.

As such, it can be appreciated that there exists a continuing need for new and improved therapeutic heating devices which are designed for use around and about a patient's head with the patient being selectively able to determine the areas of heat application, and in this respect, the present invention substantially fulfills this need.

SUMMARY OF THE INVENTION

In view of the foregoing disadvantages inherent in the known types of therapeutic heating devices now present in the prior art, the present invention provides an improved therapeutic heating device wherein the same functions both as a pillow and a source of therapeutic heat. As such, the general purpose of the present invention, which will be described subsequently in greater detail, is to provide new and improved therapeutic heating device which has all the advantages of the prior art therapeutic heating devices and none of the disadvantages.

To attain this, the present invention provides for various embodiments of fluid-filled pillows wherein the fluids can be heated to a desired temperature. In the first embodiment of the invention, the pillow includes a waterproof electric heating coil embedded therein which operates to heat the sealed fluid under the control of a thermostat. The fluid may be water, or some other liquid, or could even be a gel whose degree of softness is regulated by temperature.

In a second embodiment of the invention, the pillow is formed from a pair of flexible casings—one within the other—and being separated by a compressible electrically conductive foam material having a high electrical resistance in its uncompressed state. The facing surfaces of the casings are coated with highly electrically conductive material so that a compression of the foam, as would be occasioned by a patient laying his head upon the pillow, will result in an electric current flow between the casings. This electric current flow activates an encased heating coil contained within the sealed pillow, thereby to heat the enclosed liquid or gel.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved therapeutic heating device which has all the advantages of the prior art therapeutic heating devices and none of the disadvantages.

It is another object of the present invention to provide a new and improved therapeutic heating device which may be easily and efficiently manufactured and marketed.

It is a further object of the present invention to provide a new and improved therapeutic heating device which is of a durable and reliable construction.

An even further object of the present invention is to provide a new and improved therapeutic heating device which is susceptible of a low cost of manufacture with regard to both materials and labor, and which accordingly is then susceptible of low prices of sale to the consuming public, thereby making such therapeutic heating devices economically available to the buying public.

Still yet another object of the present invention is to provide a new and improved therapeutic heating device which provides in the apparatuses and methods of the prior art some of the advantages thereof, while simultaneously overcoming some of the disadvantages normally associated therewith.

Still another object of the present invention is to provide a new and improved therapeutic heating device which allows a user to choose the areas of heat application to his body.

Yet another object of the present invention is to provide a new and improved therapeutic heating device which utilizes automatic temperature control and which can be activated automatically by a patient lying thereon.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENTS

Figure 1:
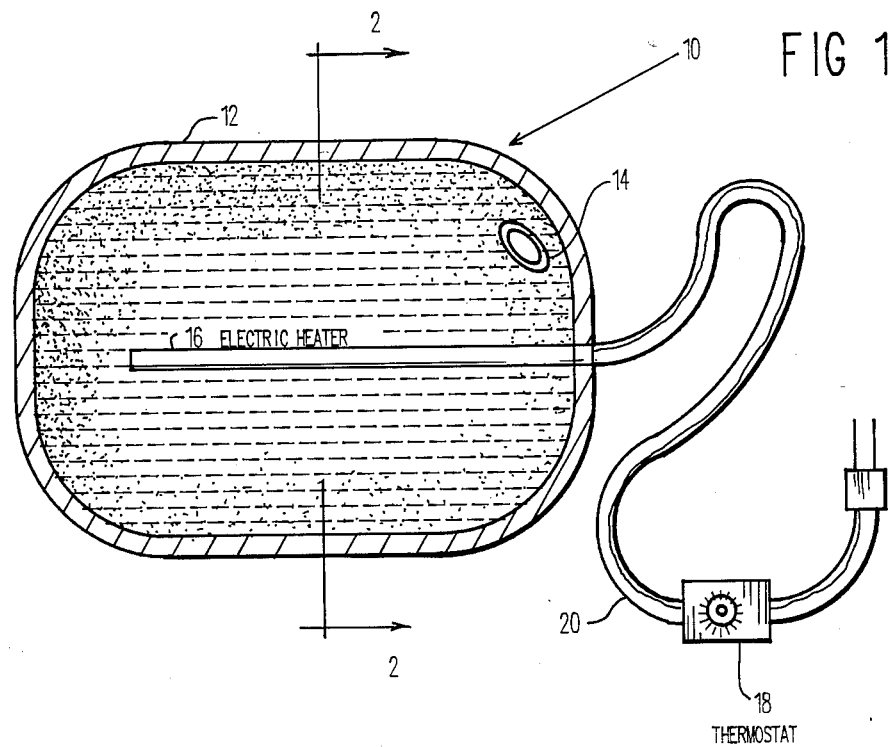
FIG. 1 is a cross-sectional view of a first embodiment of the therapeutic pillow comprising the present invention.
Figure 2:
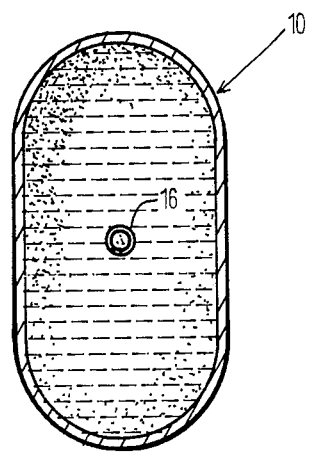
FIG. 2 is a cross-sectional view thereof taken along the line 2—2 in FIG. 1.

With reference now to the drawings, and in particular to FIGS. 1 and 2 thereof, a new and improved therapeutic pillow embodying the principles and concepts of the present invention and generally designated by the reference numeral 10 will be described.

More specifically, it will be noted that the therapeutic pillow 10 may be formed from a sealed flexible housing or casing 12, with such casing being formed from a flexible, durable material, such as plastic or the like. The casing 12 is designed to sealingly retain a fluid therein with such casing being fillable through a sealable opening 14. The casing 12 also sealingly encapsulates a heating coil 16. The heating coil 16 is of a conventional design to include an external waterproof casing wrapped about its heating portion, whereby the coil may be retained within a liquid for the purpose of heating the same.

To control the temperature within the pillow casing 12, the heating coil 16 is provided with a thermostat 18 that is attached in a conventional manner to the electric power supply line 20. As such, a user of the therapeutic pillow 16 may select a desired temperature by means of the thermostat 18, whereby the heating coil 16 will then heat a fluid contained within the casing 12 to a desired temperature. While water is the envisioned fluid to be utilized within the pillow 10, it is also within the intent and purview of the invention to utilize any known heat-retaining fluid which would permit the invention to function in its desired manner. Such fluids could include the use of a gel-like material which would become more soft as its temperature rises. As such, a dual temperature and comfort function could then be performed by the pillow 10, whereby the user could select the desired comfortable temperature and also a desired degree of softness.

Figure 3:
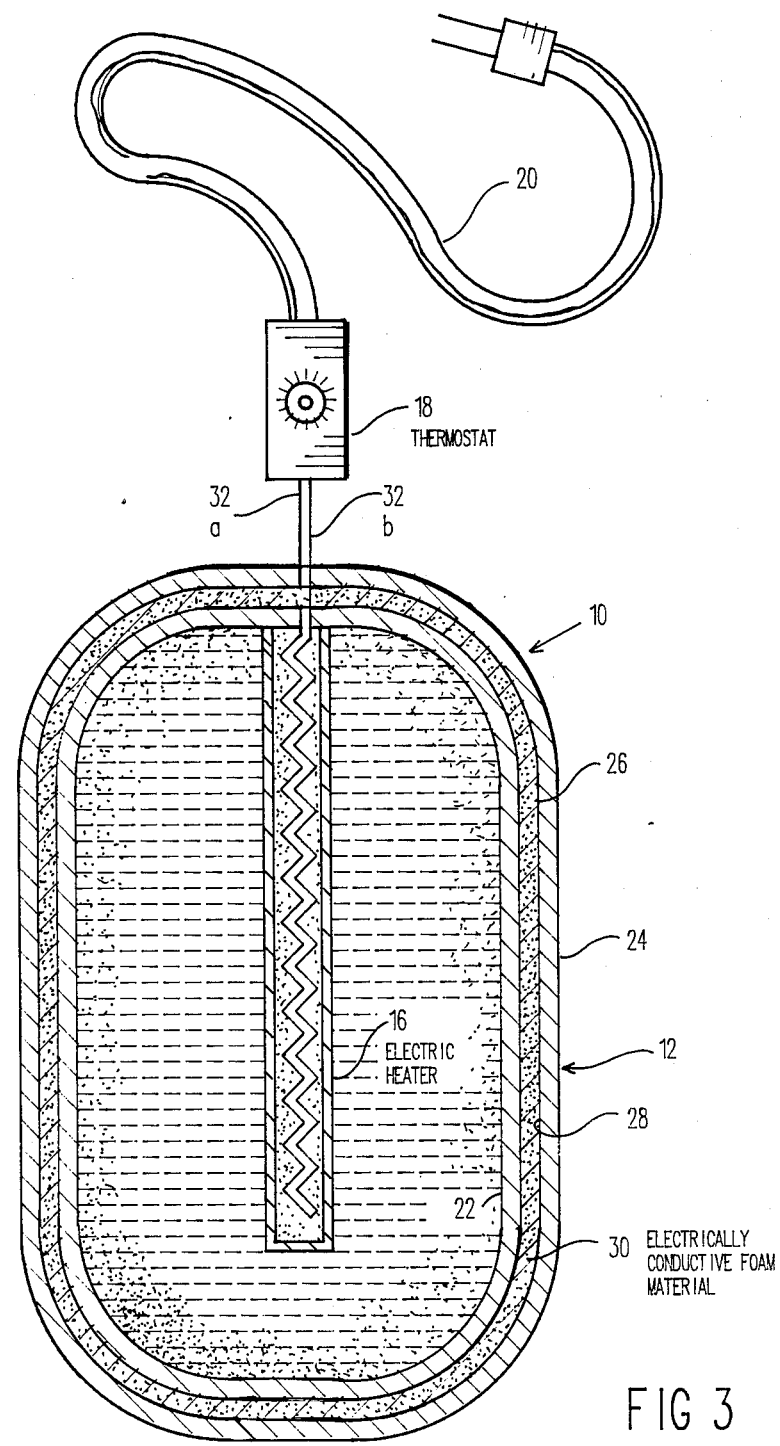
FIG. 3 is a cross-sectional view of a second embodiment of the invention.
Figure 4:
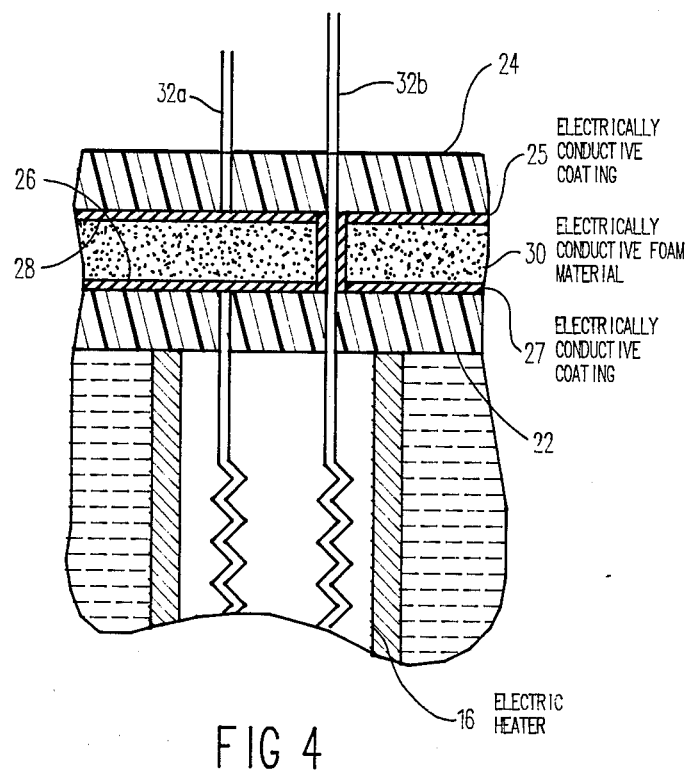

FIG. 3 of the drawings illustrates a modified embodiment of the therapeutic pillow 10, with this embodiment also including a casing structure 12, a heating coil 16 sealingly encapsulated within the casing 12, and a thermostatic control means 18 operably attached to the power supply line 20. The particular novelty in this embodiment of the invention includes a modification of the casing 12 whereby the same essentially comprises a pair of flexible casings 22, 24. The electrically nonconductive casing 22 is contained within the casing 24, and an exterior surface 26 of the casing 22 is coated with a flexible, electrically conducted material, such as aluminum or the like. Similarly, an interior surface 28 of the casing 24 is coated with a flexibly moveable, compressible electrically conductive material while the space between the surfaces 26, 28 is filled with a electrically conductive foam material 30.

FIG. 3 illustrates the way in which electrical current to the heating element is regulated. The heating element 16 has one of its terminals directly connected to the power supply through power lead 32b, which is electrically insulated from the coatings on the surfaces 26 and 28 and from the foam layer 30. The other terminal of the heating element 16 is electrically connected to the electrically conductive coating on surface 26. When the pillow, and therefore the foam layer 30, is in an uncompressed state, the resistance of layer 30 is too high to allow current to flow through it from power supply lead 32a. However, when a patient places his head on the pillow 30, the layer 30 is compressed, its electrical resistance decreases, and current can flow between the electrically conducting coating on surfaces 26, 28. While such electrical flow exists between the surfaces 26, 28, power will be supplied to the electric heating coil 16, thereby to heat the fluid contained within the therapeutic pillow 10.

With respect to the manner of use and operation of the present invention, the same should be apparent from the above description. Accordingly, no further discussion of such use and operation appears to be necessitated.

With respect to the above description then, it is to realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A therapeutic heating device, comprising:
   a. flexible housing means forming a pillow, said flexible housing means comprising first and second casings, said second casing being retained within said first casing with a space being defined therebetween, said first casing having an inner surface coextensively coated with a highly conductive flexible material, said second casing having an outer surface coextensively coated with a highly conductive flexible material, said space being filled by an electrically conductive foam, said foam having very high resistance in an uncompressed state and very low resistance in a compressed state, said foam being in coextensive electrical contact with said material coating said outer surface of said inner casing and said material coating said inner surface of said outer casing;

b. fluid means sealingly contained within said inner casing;
c. electric heating means disposed in said second casing, said heating means being operably controlled by a thermostat means, said heating means having first and second terminals, said second terminal being electrically connected to said conductive material coating said outer surface of said second casing; and
d. power supply means for operating said electric heating means, a first lead of said power supply means being electrically connected directly to said first terminal of said heating means, said first lead being electrically insulated from said electrically conductive coatings and said foam, a second lead of said power supply being electrically connected to said conductive material coating said inner surface of said outer casing, so that pressure applied to the outer surface of said first casing will cause said foam to assume its compressed state of low electrical resistance to complete the circuit from said second power supply lead to said second terminal of said heating means thereby causing energization of said heating means.

* * * * *